United States Patent [19]

Wilson et al.

[11] Patent Number: 4,970,068
[45] Date of Patent: Nov. 13, 1990

[54] USE OF D-CARVONE AS MOSQUITO ATTRACTANT

[75] Inventors: Richard A. Wilson, Westfield, N.J.; Jerry F. Butler, Gainesville, Fla.; Donald Withycombe, Lincroft; Braja D. Mookherjee, Holmdel, both of N.J.; Ira Katz, West Long Branch; Kenneth R. Schrankel, Tinton Falls, both of N.J.

[73] Assignees: International Flavors & Fragrances Inc., New York, N.Y.; The University of Florida, Gainesville, Fla.

[21] Appl. No.: 2,015
[22] Filed: Jan. 9, 1987
[51] Int. Cl.$^5$ .............................. A61K 49/00
[52] U.S. Cl. .................................. 424/84
[58] Field of Search ........................ 424/84

[56] References Cited

PUBLICATIONS

Boroza et al., "Materials Tested as Insect Attractants" Agricultural Handbook No. 239, Agricultural Research Service, USDA (1963).

Primary Examiner—Douglas W. Robinson
Attorney, Agent, or Firm—Arthur L. Liberman

[57] ABSTRACT

Described is the use of d-carvone having the structure:

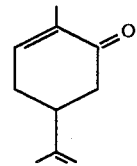

as an attractant for mosquitos (Culicidae). The d-carvone finds utility primarily as a bait enhancer for acute toxins and/or trapping devices.

1 Claim, 4 Drawing Sheets

USE OF D-CARVONE AS MOSQUITO ATTRACTANT

BACKGROUND OF THE INVENTION

This invention relates to an attractant for Culicidae (mosquitos). More particularly this invention relates to compositions of matter containing d-carvone as an attractant for Culicidae.

Fast intercontinental travel and trade are stepping up chances of importing nonindigenous insect pests into the United States. Attractants, or lures, can be of considerable aid in facilitating the early detection of such insect pests, and they are of vital importance in measuring the progress of a program aimed at eradicating a species that has become established.

In Agriculture Handbook No. 239 published by the Agricultural Research Service of the United States of America Department of Agriculture issued in June 1963 entitled, "Materials Tested As Insect Attractants", compiled by M. Beroza and N. Green carvone (Item 2656) having the structure:

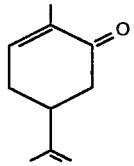

is indicated to have an attractancy of "1" on a scale of 1 to 3 for the Oriental Fruit Fly, the Mexican Fruit Fly and the Mediterranean Fruit Fly; but is not indicated to show any attractancy for the mosquito.

Menthone having the structure:

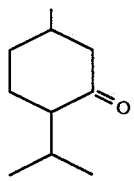

(Item No. 2688) is indicated in Agriculture Handbook No. 239 to have an attractancy for the Oriental Fruit Fly, the Melon Fly, the Mediterranean Fruit Fly and the Mexican Fruit Fly of "1" on a scale of 1 to 3 but is not shown to have any attractancy for the mosquito.

Gunderson, et al, *Pestic. Biochem. Physiol*, 1986, at No. 166860s, 26(2), 238–49, "Microsomal oxidase and glutathione transferase as factors influencing the effects of pulegone in southern and fall armyworm larvae" discloses the fact that pulegone is 3.5–4 times more toxic acutely, to southern armyworm, *Spodoptera eridania* than to fall armyworm, *S. frugiperda* larvae.

However, nothing in the prior art discloses the use of d-carvone having the structure:

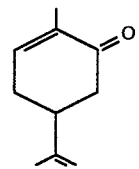

as useful in attracting Culicidae

SUMMARY OF THE INVENTION

Figure 1:
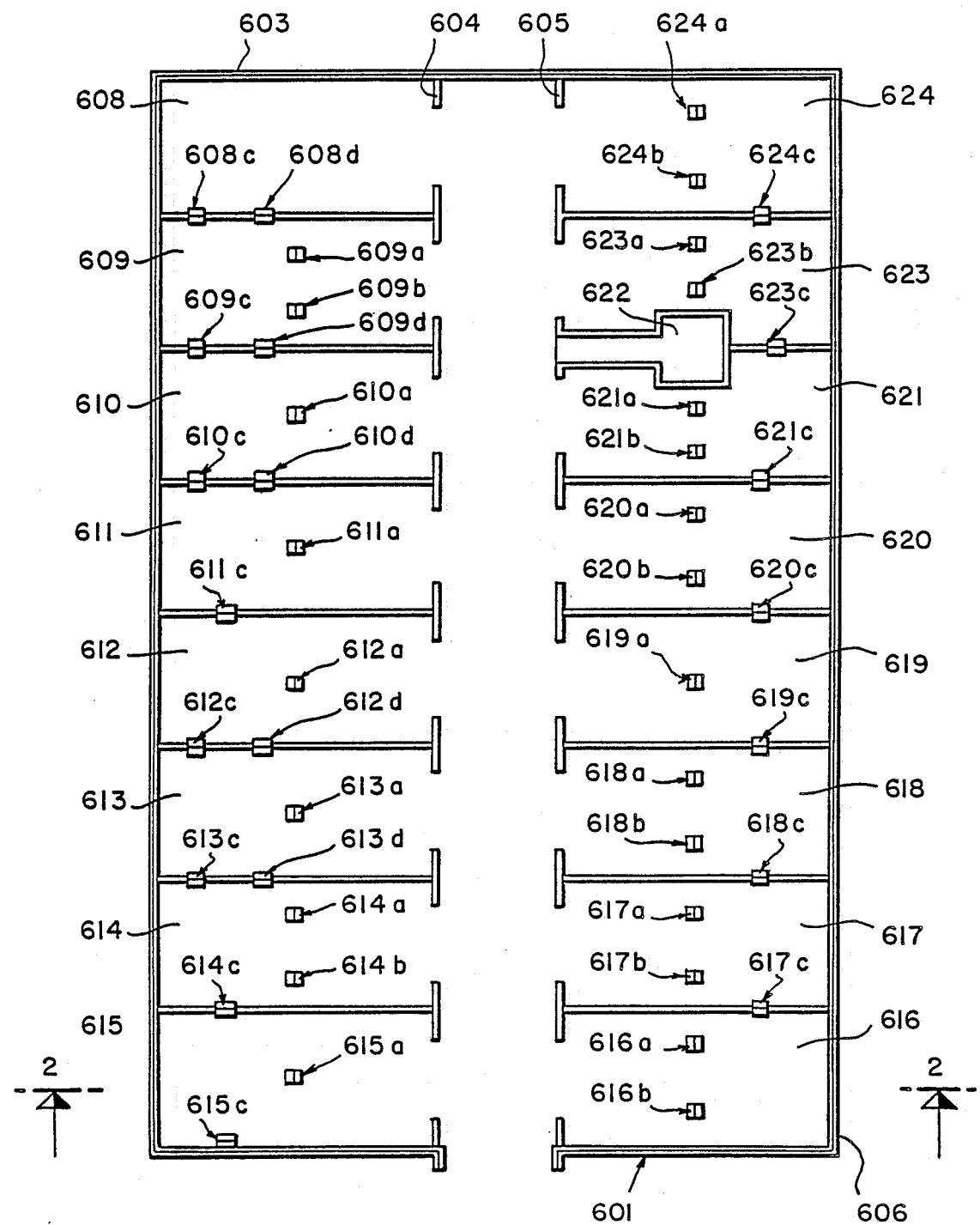
FIG. 1 is a schematic top view of the location of insect traps containing formulated slow release mosquito attractants and control materials (known attractant, GOLDEN MALRIN ® insect bait).
Figure 2:
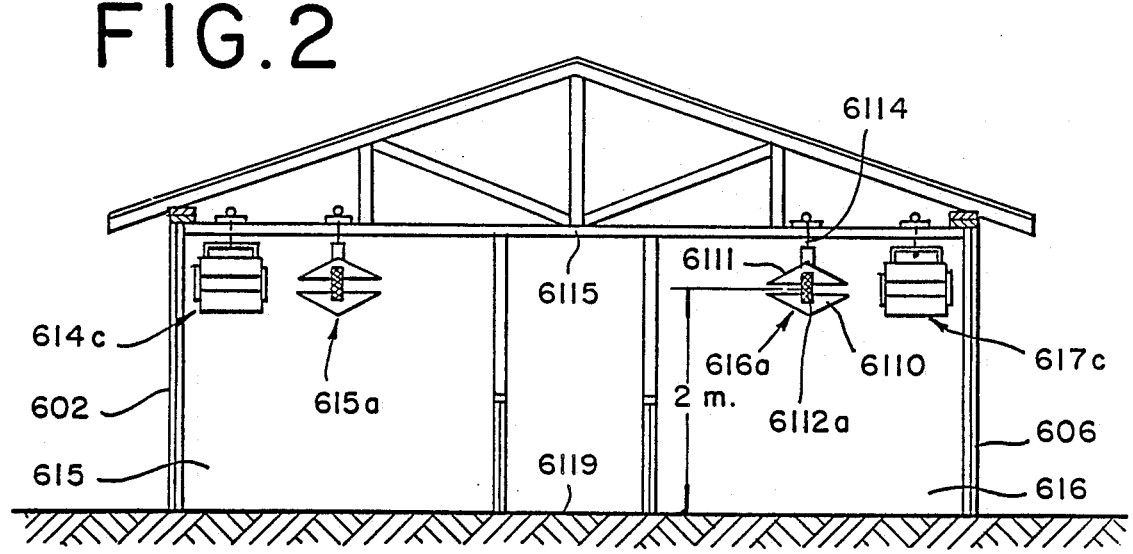
FIG. 2 is a cut-away side elevation view (schematic) indicating the positioning of sticky traps in a test barn taken along lines 2—2 of FIG. 1.
Figure 3:
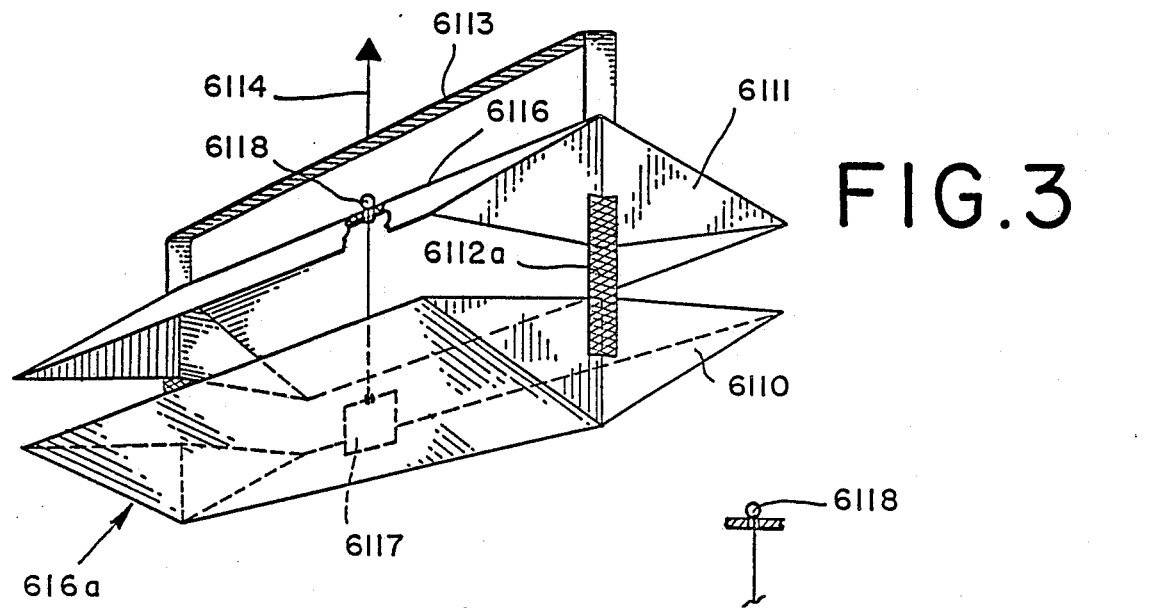
FIG. 3 is a perspective schematic view of a test sticky trap showing the positioning of the slow release material suspended inside of the trap structure.
Figure 4:
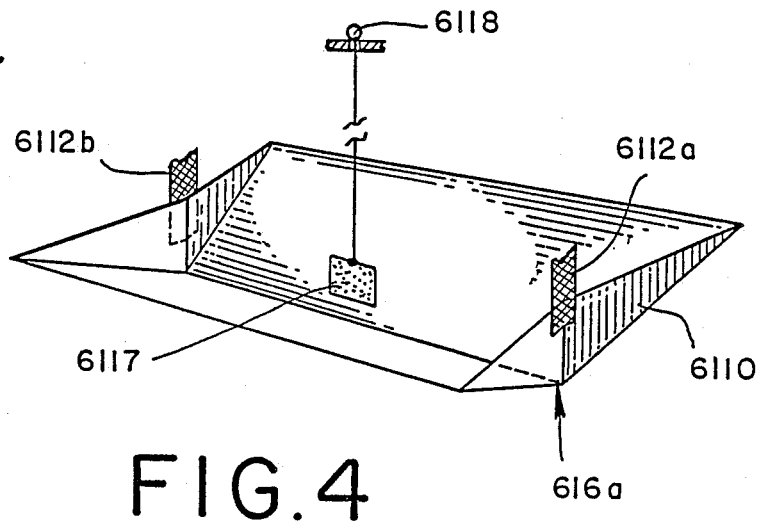
FIG. 4 is a cut-away section in perspective of the sticky trap system of FIG. 3.

Our invention relates to the use of d-carvone as an attractant for mosquitos (Culicidae).

The trapping system used in testing the efficacy of the d-carvone is a standard ZOECON ® sticky trap consisting of a ZOECON PHEROCON ® 1C trap with a 2 cm x 2 cm strip (or "lamina") of formulated slow release attractant (in an amount sufficient to attract mosquitos from the three-space surrounding the lamina) suspended on a paper clip inside the trap. The traps were placed in a goat barn and are suspended from the rafters. Trap placement was replicated in the four quadrants of the barn. Traps were placed in the barn for seven days and the mosquitos collected were identified and counted. All test materials were compared with a standardized check treatment consisting of 0.5 grams of GOLDEN MALRIN ® insect bait inside of the slow release packet hung like the other compounds.

Our invention also relates to the formation of mosquito attractant-containing polymeric pellets by means of introduction into a single screw or twin screw extruder of, in series, thermoplastic polymer followed by mosquito attractant which is compatible with the thermoplastic polymer, in turn, followed by introduction of a gaseous blowing agent or blowing agent which will produce a gas which is inert to the polymer and to the mosquito attractant, e.g., d-carvone.

In the alternative, the use of the foaming agent can be omitted.

The nature of the extruder utilized in this aspect of our invention to form the polymeric mosquito attractant particles of our invention may be either single screw or double screw. Thus, the types of extruder that can be used are disclosed at pages 246–267 and 332–349 of the Modern Plastics Encyclopedia, 1982–1983 published by the McGraw-Hill Publishing Company, the disclosure of which is incorporated by reference herein. More specifically, examples of extruders which are usable in carrying out this aspect of our invention (with modification for introduction of mosquito attractant downstream from introduction of the polymer and optionally with a further modification that the gaseous blowing agent is introduced still further downstream from the point of introduction of insect attractant) are as follows:

1. The Welex "Super Twinch" 3.5Δ extruder manufactured by Welex Incorporated, 850 Jolly Road, Blue Bell, Pa. 19422;
2. Krauss-Maffei twin screw extruder manufactured by the Krauss-Maffei Corporation/Extruder Division, 3629 West 30th Street South, Wichita, Kans. 67277;
3. Modified Sterling model 4000 and 5000 series extruder manufactured by Sterling Extruder Corporation of 901 Durham Avenue, South Plainfield, N.J.;
4. CRT ("Counter-Rotating Tangential") Twin Screw Extruder manufactured by Welding Engineers, Inc. of King of Prussia, Pa. 19406;
5. The Leistritz Twin Screw Dispersion Compounder manufactured by the American Leistritz Extruder Corporation of 198 U.S. Route 206 South, Somerville, N.J. 08876;
6. The ZSK Twin Screw Co-Rotating Extruder manufactured by the Werner & Pfleiderer Corporation of 663 East Crescent Avenue, Ramsey, N.J. 07446;
7. The Farrel Extruder manufactured by Farrel Connecticut Division, Emhart Machinery Group, Ansonia, Conn. 06401;
8. The MPC/V Baker Perkins Twin Screw Extruder manufactured by the Baker Perkins Inc. Chemical Machinery Division of Saginaw, Mich. 48601; and
9. The Berstorff single screw, twin screw, or foam extrusion equipment manufactured by Berstorff Corporation, P.0. Box 240357, 8200-A Arrowridge Blvd., Charlotte, N.C. 28224.

In producing the mosquito attractant-containing polymer particles of our invention, various polymers may be utilized, for example, low density polyethylene, high density polyethylene, polypropylene, the co-polymer of ethylene and vinyl acetate, and polyvinyl chloride. More specifically, the polymers used in the practice of our invention may be co-polymers of ethylene and a polar vinyl monomer selected from (a) vinyl acetate; (b) ethyl acrylate; (c) methyl acrylate; (d) butyl acrylate and (e) acrylic acid including the hydrolyzed co-polymer of ethylene and vinyl acetate. Preferred co-polymers are ethylene vinyl acetate with about 9 to 60% vinyl acetate and ethylene/ethyl acrylate with about 6 to 18% ethyl acrylate.

Resins of the type disclosed for use as co-polymers are commercially available in the molding powder form. For example, ethylene vinyl acetate co-polymers are marketed by the E.I. duPont de Nemours Company under the tradename "ELVAX®" and by the Arco Polymer Division under the trademark "DYLAND®" and by the Exxon of Corporation of Linden, N.J. under the trademark "DEXXON®". Ethylene/ethyl acrylate co-polymers are marketed by Union Carbide Corporation under the tradename "EEA RESIN®".

The polymer is added to the single screw or twin screw extruder at a feed rate in the range of from about 80 up to about 300 pounds per hour while maintaining the temperature in the screw extruder between about 160° and about 240° C. If the polymer or co-polymer powder is added to the extruder at a reference "barrel segment", then the mosquito attractant is added to the extruder under pressure downstream from the addition point of the polymer at 1 or more "barrel segments" S-2, S-3, S-4, S-5, S-6, S-7, S-8 or S-9 (shown in FIG. 6).

Thus, the invention provides a process for forming mosquito attractant-containing polymeric particles such as polymeric pellets which include a relatively high concentration of mosquito attractant. The mosquito attractant added at "barrel segments" S-2, S-3, S-4, S-5, S-6, S-7, S-8 or S-9 of the single screw or twin screw extruder is to be compatible with the polymer added at "barrel segment" S-1 of the single screw or twin screw extruder.

The proportion of mosquito attractant is limited only by either (a) its solubility in the resin or mixture of resins used and/or (b) the volume ratio of microvoids in the polymer to said polymer and/or (c) the solubility of the mosquito attractant in the polymer on solidification. The proportion of mosquito attractant can in many instances go up to 45% by weight or even higher.

Thus, the proportion of mosquito attractant to resin can vary from small but effective amounts on the order of about 1% of the weight of the resin body up to about 45% by weight of the resin body. In general, it is preferred to use between about 5% up to about 30% based on the weight of resin body of the mosquito attractant. This is an optimum amount balancing the proportion of mosquito attractant against the time period over which the article emits the mosquito attractant and against the tendency of the mosquito attractant to "oil out". This "oiling out" is specifically avoided as a result of the use of foaming agent.

As stated, supra, various polymers are useful in the practice of our invention. Specific examples of polymers useful in the practice of our invention are as follows:

(a) DYLAN ® brand of low density polyethylene DYLAN ® is a trademark owned by the Atlantic Richfield Company of Los Angeles, Calif.;
(b) DYLITE ® of expandable polystryene compositions. DYLITE ® is a trademark of the Atlantic Richfield Company of Los Angeles, Calif.;
(c) SUPER DYLAN ® a high density polyethylene. SUPER DYLAN ® is a trademark of the Atlantic Richfield Company of Los Angeles, Calif.;
(d) Blended polyethylene and carbon black as specifically taught in U.S. Pat. No. 4,369,267 issued on Jan. 18, 1983, the specification for which is incorporated by reference herein;
(e) Polystyrene as disclosed in U.S. Pat. No. 4,369,227 issued on Jan. 18, 1983, the specification for which is incorporated by reference herein;
(f) Polyene/alpha-olefin as exemplified and disclosed in U.S. Pat. No. 4,369,291, the specification for which is incorporated by reference herein;
(g) Poly-alpha-olefins as exemplified in Canadian Letters Patent No. 1,137,069 issued on Dec. 7, 1982, the specification for which is incorporated by reference herein;
(h) Polymeric compositions as disclosed in Canadian Letters Patent No. 1,137,068 issued on Dec. 7, 1982, the specification for which is incorporated by reference herein;
(i) Poly-alpha-olefins disclosed in Canadian Letters Patent No. 1,137,067, the specification for which is incorporated by reference herein;
(j) Polyolefins described in Canadian Letters Patent No. 1,137,066, the specification for which is incorporated by reference herein;
(k) Polyethylene oxides as disclosed in Canadian Letters Patent No. 1,137,065 issued on Dec. 7, 1982, the specification for which is incorporated by reference herein;
(l) Olefin polymers and co-polymers as disclosed in Canadian Letters Patent No. 1,139,737, the disclosure of which is incorporated by reference herein Canadian Patent No. 1,139,737 was issued on Jan. 18, 1983;
(m) Polyolefins disclosed in Canadian Letters Patent No. 1,139,738, the disclosure of which is incorporated by reference herein. Canadian Patent No. 1,139,738 was issued on Jan. 18, 1983;
(n) Chlorinated PVC as disclosed in Polymer 1982, 23 (7,Suppl.), 1051-6 abstracted at Chem. Abstracts 97:145570y, 1982;
(o) Polyepsilon caprolactone co-polymers made by means of alcohol initiated polymerization as disclosed in *J. Polym. Sci.* Polym. Chem. Ed. 1982, 20(2), pages 319–26, abstracted at Chem. Abstracts, Volume 96:123625x, 1982;
(p) Styrene acrylonitrile co-polymers as disclosed in Diss. Abstracts, Int. B, 1982, 42(8), 3346 and abstracted at Chem. Abstracts 96:143750n (1982);
(q) Co-polymers of epsilon caprolactone with 1,4-butane diol as disclosed at Kauch. Rezine, 1982, (2), 8–9, abstracted at Chem. Abstracts, Volume 96:182506g (1982);
(r) Polyesters as disclosed in U.S. Pat. No. 4,326,010, the specification for which is incorporated by reference herein;
(s) Chlorinated polyethylene as disclosed by Belorgey, et al., *J. Polym. Sci.* Polym. Phys. Ed. 1982, 20(2), 191–203;
(t) Plasticized polyepsilon caprolactone co-polymers containing dimethyl phthalate plasticizers as set forth in Japanese Pat. No. J81/147844, abstracted at Chem. Abstracts, Volume 96:69984y (1982), the specification for which is incorporated by reference herein;
(u) Maleic anhydride modified adducts of polyepsilon caprolactone polyols and ethylenically unsaturated monomer as disclosed in U.S. Pat. No. 4,137,279 issued on Jan. 30, 1979, the specification for which is incorporated by reference herein;
(v) Polyurethane polymers having lactone backbones as disclosed in U.S. Pat. No. 4,156,067 issued on May 22, 1979, the disclosure of which is incorporated by reference herein;
(w) Polyurethane polyether resins wherein the resin is obtained by reacting a polyfunctional lactone with a long chain polyalkylene diol and a urethane precursor as disclosed in U.S. Pat. No. 4,355,550 issued on Mar. 10, 1981, the disclosure of which is incorporated by reference herein; and
(x) Resins having polyurethane backbones as disclosed in U.S. Pat. No. 3,975,350 issued on Aug. 17 1976, the disclosure of which is incorporated by reference herein.

Optionally, downstream from the addition point of the mosquito attractant a gaseous or liquid containing blowing agent may be added (e.g., at barrel segments S-5, S-6, S-7, S-8 or S-9 and S-10) using the polymer addition barrel segment as a reference barrel segment "S-1". Examples of gaseous blowing agents are carbon dioxide, nitrogen, mixtures of nitrogen and carbon dioxide in proportions of from 1 up to 99% by volume nitrogen and 99 down to 1% by volume carbon dioxide, helium, mixtures of helium and nitrogen, mixtures of helium and carbon dioxide and other gases which are inert at the temperature and pressure of the polymer at the time of the extrusion operation. Thus, gas containing oxygen or other reactive gases, e.g., hydrogen, should be avoided. The pressure of the gas blowing agent being added to the extruder at the point of addition may vary from about 80 up to about 150 psig. Higher pressures may be used without adversely affecting the usefulness of the foamed mosquito attractant-containing polymer particle.

The feed rate range of mosquito attractant may be between about 0.5% up to about 45% by weight of the polymer.

The die of the extruder may create rod, sheet, film or ribbon. The resulting product may then, if desired, be pelletized to form foamed mosquito attractant-containing polymer particles or the ribbon may be used "as-is" as an mosquito attractant-containing polymeric article of manufacture itself.

In addition to the optional gaseous blowing agents (which are necessarily "inert" gases), blowing agents may be added at some point on the extruder which will create gaseous voids in the mosquito attractant-containing polymeric articles of our invention and these "blowing agents" are well known to one having ordinary skill in the art. Examples of such non-gaseous containing materials which yield gases on admixture with the polymer in the extruder but which are still inert to the mosquito attractant are as follows:
(i) Under high pressure, ethylene, methane, propane, butane, propylene, methyl chloride, methyl bromide, vinyl chloride and methylene dichloride as more specifically described in U.S. Pat. No. 2,387,730, the specification for which is incorporated by reference herein;
(ii) Ordinarily liquid material such as n-pentane, iso-pentane, cyclopentane, hexane and petroleum ether fractions or halogen hydrocarbons such as $CFCl_3$, $CF_2Cl_2$, $CH_3Cl$, $CH_2Cl_2$ separately or in admixture with one another as set forth in U.S. Pat. No. 3,758,425, column 4, lines 1–5, the specification for which is incorporated by reference herein;
(iii) Dichlorotetrafluoroethane, tetramethylmethane, monochlorodifluoromethane, dichlorodifluoromethane, and dichlorotetrafluoroethane as specifically described in U.S. Pat. Nos. 2,948,664 and 2,948,665 issued on Aug. 9, 1960, the specifications for which are incorporated herein by reference; and
(iv) Azo bis(formamide); diazoaminobenzene; N,N'-dinitrosopentamethylene tetramine; N,N'-dimethyl-N,N'-dinitrosoterephthalamide; p,p'-oxy-bis(-benzene sulfonyl semicarbazide); azo bis-(isobutyronitrile); p,p'-oxy-bis(benzene sulfonyl hydrazide); p,p'-diphenyl-bis(sulfonyl hydrazide); benzene-sulfonyl hydrazide; m-benzene-bis(sulfonyl hydrazide) as more specifically described in U.S. Pat. No. 3,298,975 issued on Jan. 17, 1967, the specification for which is incorporated by reference herein.

The resulting extruded (and if desired pelletized) material may then be for example injection molded to form a useful article. Such injection molding can be carried out in accordance with the procedure as set forth in U.S. Pat. No. 3,268,636 issued on Aug. 23, 1966, the specification for which is incorporated by reference herein.

DETAILED DESCRIPTION OF THE DRAWINGS

Referring to FIGS. 1, 2, 3 and 4, FIGS. 3 and 4 show in detail the ZOECON ® sticky trap, more specifically a ZOECON PHEROCON ® 1C Trap (e.g., in FIG. 4 indicated by reference numeral 616a) and in FIG. 1 indicated by reference numerals 608c, 608d, 609a, 609b, 609c, 609d, 610a, 610c, 610d, 611a, 611c, 612a, 612c, 612d, 613a, 613c, 613d, 614a, 614b, 614c, 615a, 615c, 616a, 616b, 617a, 617b, 617c, 618a, 618b, 618c, 619a, 619c, 620a, 620b, 620c, 621a, 621b, 621c, 623a, 623b, 623c, 624a, 624b and 624c. The ZOECON PHEROCON ® 1C Trap has suspended in it as will be seen from FIGS. 3 and 4, a 2 cm x 2 cm strip (or lamina) of slow release polymer (polyethylene) 6117 in FIGS. 3 and 4 containing mosquito attractant (d-carvone) in an amount sufficient to attract Culicidae (mosquitos) or the 2 cm x 2 cm strip contains the GOLDEN MALRIN ® control. The 2 cm x 2 cm strip 6117 is suspended in the trap 616a from apex 6116 using holder 6118. Trap 616a has lower tray 6110 which will catch dead mosquitos which do not adhere to the 2 cm x 2 cm strip 6117. The lower tray 6110 is attached via strips 6112a and 6112b to upper holder 6111 which is attached to suspension bar 6113 suspended by rod 6114 to the barn beam 6115 (in FIG. 2). The barn beam 6115 is held in a horizontal position by upright supports 602 and 606 (as will be seen in FIG. 2) which is firmly in place on the barn floor 6119. The 2 cm x 2 cm strip 6117 is formulated in such apparatus as is set forth in FIG. 6 described in detail, infra. The traps containing the mosquito attractant, e.g., d-carvone or the GOLDEN MALRIN ® control are placed in the goat barn having fencing panels 601 and 603 and inner support 604 and 605, an observation post 622 and experimental locations 608, 609, 610, 611, 612, 613, 614, 615, 616, 617, 618, 619, 620, 621, 623, and 624 has suspended in it the several ZOECON PHEROCON ® 1C Traps each containing 2 cm x 2 cm strips of formulated slow release mosquito attractants. Trap placement was replicated in four quadrants of the barn. Traps 616a, 616b, 615a, 615c and other traps were placed in the barn for seven days and the mosquitos collected were identified and counted. All the test materials were compared with a standardized check treatment consisting of 0.5 grams of GOLDEN MALRIN ® insect bait inside slow release packets hung like the other compounds as in strip 6117 in FIGS. 3 and 4.

Figure 5:
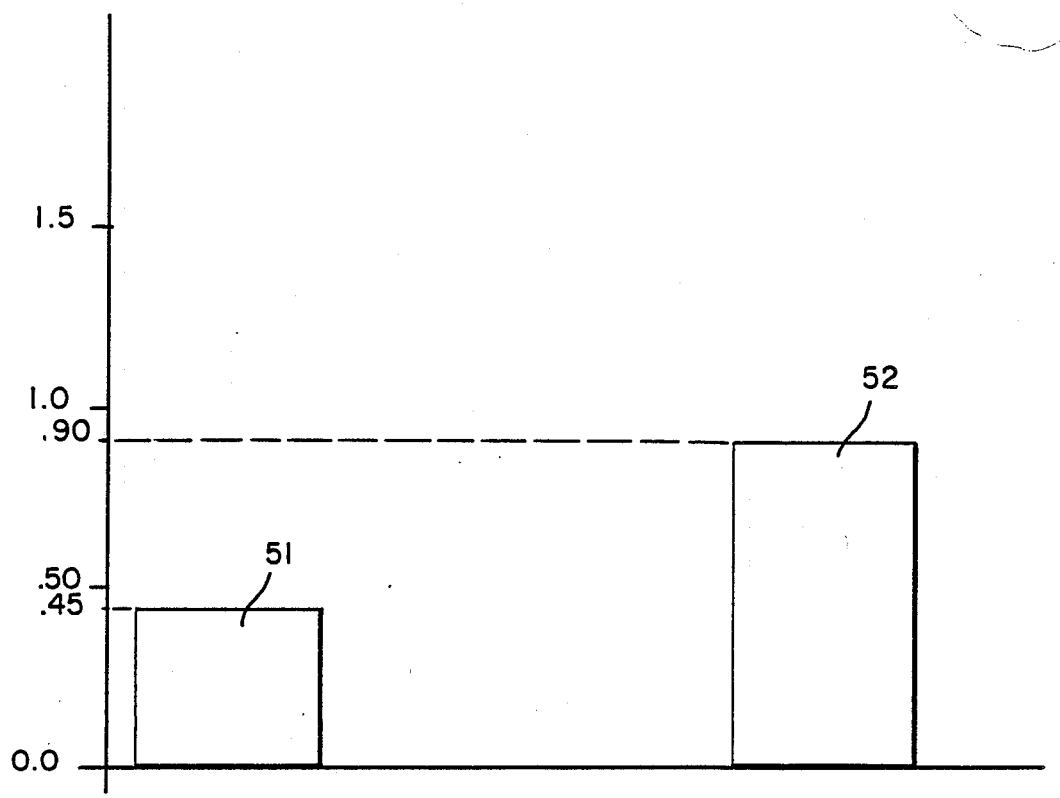
FIG. 5 is a bar graph showing a comparison of the field trial tests of attractants for Culicidae (mosquitos) comparing d-carvone and GOLDEN MALRIN ®, a mixture of (Z)-9-tricosene and methomyl which is methomyl(s-methyl N-[methylcarbamoyl]oxy)thioacetimidate the graph being compound vs mosquitos/trap.

FIG. 5 indicates the results of field trial tests using the apparatus set forth in FIGS. 1, 2, 3 and 4.

FIG. 5 sets forth field trial tests for the attractants d-carvone and GOLDEN MALRIN ® insofar as their attractancy for Culicidae (mosquitos). FIG. 5 is a bar graph. The bar graph indicated by reference numeral 52 is the bar graph for d-carvone insofar as it attracts Culicidae (mosquitos). The bar graph indicated by reference numeral 51 is the bar graph for GOLDEN MALRIN ® (insofar as it attracts Culicidae (mosquitos)). FIG. 5 is a graph of mosquitos/trap vs compound. Thus, the d-carvone in FIG. 5 gives rise to an attractancy of Culicidae of 0.90 mosquitos per trap; and the GOLDEN MALRIN ® gives rise to only 0.45 mosquitos per trap.

Figure 6:
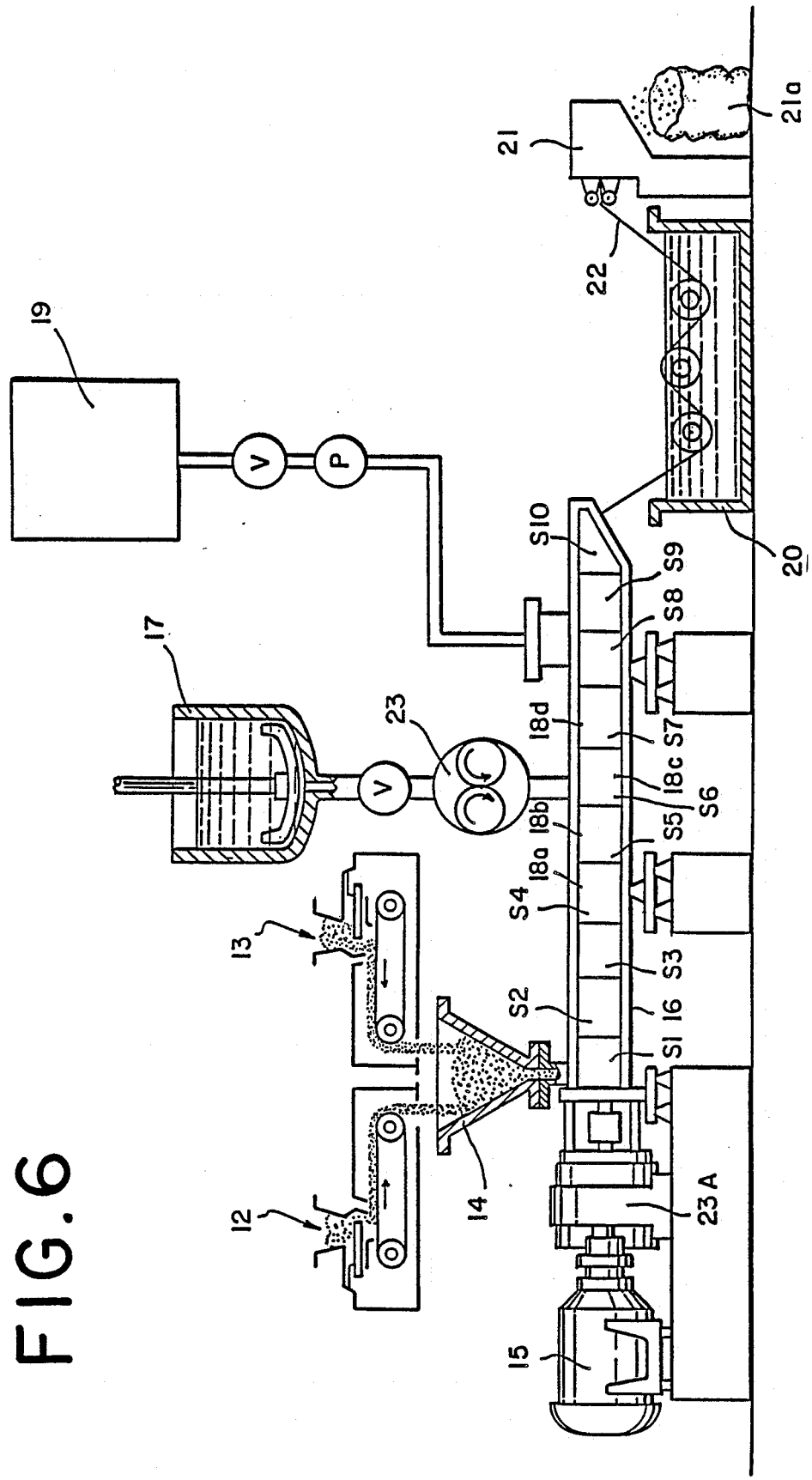
FIG. 6 is a cut-away side elevation schematic diagram of a screw extruder during the compounding of a resin with the mosquito attractant d-carvone while simultaneously adding foaming agent into the hollow portion of the barrel of the extruder and incorporates the pelletizing apparatus used in pelletizing the extruded foamed tow produced as a result of the extrusion operation.

FIG. 6 is a schematic cut-away elevation diagram of an extrusion and pelletizing apparatus useful in carrying out a process of our invention during the operation of said apparatus whereby the mosquitos attractant is incorporated into a polymer such as a polyethylene. Motor 15 drives the extruder screws located at 23A in barrel 16, the extruder being operated at temperatures in the range of about 150° up to about 250° C. At the beginning of the barrel resin at source 12 together with additives, e.g., processing aids and densifiers at location 13 is added via addition funnel 14 into the extruder. Simultaneously (when the operation reaches "steady state"), mosquito attractant, d-carvone is added to the extruder at one, two or more of barrel segments S-3, S-4, S-5, S-6, S-7 and S-8 of the extruder (which may be a twin screw or single screw extruder) at locations 18a, 18b, 18c and 18d (for example) by means of gear pump 23 from source 17. From source 19 into barrel segments S-5, S-6, S-7, S-8, S-9 and S-10, a gaseous or liquid blowing agent, e.g., nitrogen, carbon dioxide and the like as described, supra, are added simultaneously with the addition of the mosquito attractant, e.g., d-carvone. The feed rate range of resin is about 80-300 pounds per hour. The feed rate range of the mosquito attractant is between 1 and 35% of the feed rate range of the resin. The blowing agent rate range is such that the pressure of the gas or the pressure over the liquid being fed into the extruder is between about 50 and 200 psig if, indeed, blowing agent is added. If desired, the extruded ribbon or cylinder may be passed through water bath 20 and pelletizer 21 into collection apparatus 21a.

What is claimed is:

1. A method of attracting Culicidae to an insect trap comprising the step of exposing the environment surrounding said trap to an insect attractant containing polymer which consists of a mixture of a polymer and from about 1% up to about 45% by weight of said polymer of d-carvone.

* * * * *